US006627076B2

(12) United States Patent
Griffiths

(10) Patent No.: US 6,627,076 B2
(45) Date of Patent: Sep. 30, 2003

(54) COMPACT MICROCHANNEL SYSTEM

(75) Inventor: Stewart Griffiths, Livermore, CA (US)

(73) Assignee: Sandia National Laboratories, Livermore, CA (US)

( * ) Notice: Subject to any disclaimer, the term of this patent is extended or adjusted under 35 U.S.C. 154(b) by 84 days.

(21) Appl. No.: 10/039,938

(22) Filed: Oct. 19, 2001

(65) Prior Publication Data

US 2003/0075491 A1 Apr. 24, 2003

(51) Int. Cl.[7] ............................................. B01D 15/08
(52) U.S. Cl. .................... 210/198.2; 210/656; 204/601; 422/70
(58) Field of Search ................................ 204/600, 601, 204/602, 603, 604, 605, 451, 452, 453, 454, 455, 450; 210/635, 656, 659, 198.2; 422/70

(56) References Cited

U.S. PATENT DOCUMENTS

| 4,891,120 | A | * | 1/1990 | Sethi ....................... 204/299 R |
| 5,116,495 | A | * | 5/1992 | Prohaska ................. 210/198.2 |
| 5,376,252 | A | * | 12/1994 | Ekstrom et al. ......... 204/299 R |
| 5,571,410 | A | * | 11/1996 | Swedberg ................ 210/198.2 |
| 5,658,413 | A | * | 8/1997 | Kaltenbach .............. 156/272.8 |
| 5,888,390 | A | * | 3/1999 | Craig ....................... 210/198.2 |
| 5,935,430 | A | * | 8/1999 | Craig ....................... 210/198.2 |
| 6,186,660 | B1 | | 2/2001 | Kopf-Sill et al. ............ 366/340 |
| 6,258,263 | B1 | * | 7/2001 | Henderson et al. ...... 210/198.2 |
| 6,440,284 | B1 | * | 8/2002 | Dubrow ...................... 204/455 |
| 6,459,080 | B1 | * | 10/2002 | Yin ............................. 250/288 |

OTHER PUBLICATIONS

Griffiths, S. K.; Nilson, R. H.; "Low–Dispersion Turns and Junctions for Micro–channel Systems"; Anal. Chem., v. (73), Jan. 15, 2001, pp. 272–278.

Culbertson, C. T.; Jacobson, S. C.; Ramsey, J. M.; "Microchip Devices for High–Efficiency Separations"; Anal. Chem., V.(72), Dec. 1, 2000, pp. 5814–5819.

Paegel, B. M.; Hutt, L. D.; Simpson, P. C.; Mathies, R. A.; "Turn Geometry for Minimizing Band Broadening in Microfabricated Capillary Electrophoresis"; Anal. Chem., v(72), Jul., 15, 2000, pp. 3030–3037.

Zubritsky, E.; "Taming Turns in Micro channels"; Anal. Chem.; Nov. 1, 2000; pp. 687A–690A.

Griffiths, S. K.; Nilson; "Band Spreading in Two–Dimensional Microchannel Turns for Electrokinetic Species Transport"; Anal. Chem., v.(72), Nov. 1, 2000, pp. 5473–5482.

Culbertson, C. T.; Jacobson, S. C.; Ramsey, J. M.; "Dispersion Sources for Compact Geometries on Microchips"; Anal. Chem., v.(70), Sep. 15, 1998, pp. 3781–3789.

Kasicka, V.; Prusik, Z.; Gas, B. Stedry, M.; "Contribution of capillary coiling to zone dispersion in capillary zone electrophoresis"; Electrophoresis, v.(16) 1995, pp. 2034–2038.

(List continued on next page.)

*Primary Examiner*—Ernest G. Therkorn
(74) *Attorney, Agent, or Firm*—Timothy P. Evans

(57) ABSTRACT

The present invention provides compact geometries for the layout of microchannel columns through the use of turns and straight channel segments. These compact geometries permit the use of long separation or reaction columns on a small microchannel substrate or, equivalently, permit columns of a fixed length to occupy a smaller substrate area. The new geometries are based in part on mathematical analyses that provide the minimum turn radius for which column performance in not degraded. In particular, we find that straight channel segments of sufficient length reduce the required minimum turn radius, enabling compact channel layout when turns and straight segments are combined. The compact geometries are obtained by using turns and straight segments in overlapped or nested arrangements to form pleated or coiled columns.

21 Claims, 4 Drawing Sheets

OTHER PUBLICATIONS

Jacobson, S. C.; Hergenroder, R.; Koutny, L. B.; Ramsey, J. M.; "High–Speed Separation on a Microchip"; Anal. Chem., v(66), Apr. 1, 1994, pp. 1114–1118.

Effenhauser, C.; Manz, A.; Widmer, H. M.; "Glass Chips for High–Speed Capillary Electrophoresis Separations with Submicrometer Plate Heights"; Anal. Chem., v.(65), Oct. 1, 1993, pp. 2637–2642.

Harrison, D. J.; Manz, A.; Fan, Z. H.; Ludi, H.; Widmer, H. M.; "Capillary Electrophoresis and Sample Injection Systems Integrated on a Planar Glass Chip"; Anal. Chem., 1992 v.(64), pp. 1926–1932.

Manz, A.; Harrison, D. J.; Verpoorte, E. M. J.; Fettinger, J. C.; Paulus, A.; Ludi, H.; Widmer, H. M.; "Planar chips technology for miniaturization and integration of separation techniques into monitoring systems"; J. Chromatogr., v.(593), 1992, pp. 253–258.

Manz, A.; Fettinger, J. C.; Verpoorte, E.; Ludi, H.; Widmer, H. M.; Harrison, D. J. "Micromachining of monocrystalline silicon and glass for chemical analysis systems A look into next century's technology or just a fashionable craze?"; Trends Anal. Chem., v.(10), 1991, pp. 144–149.

Saffman, P. G.; "Viscous fingering in Hele–Shaw cells"; J. Fluid. Mech., v.(173), 1986, pp. 73–94.

* cited by examiner

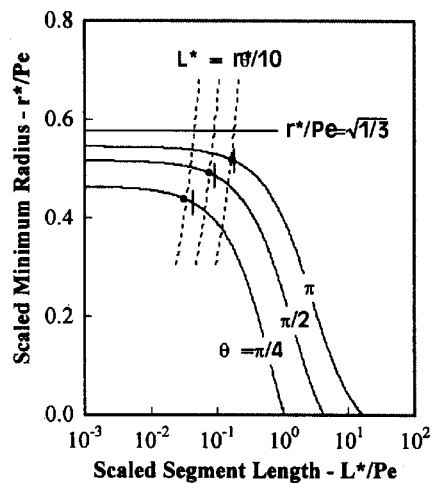
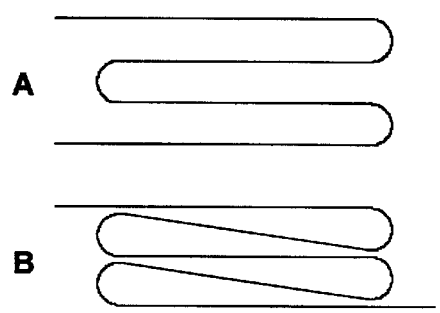
FIG. 5
FIG. 6
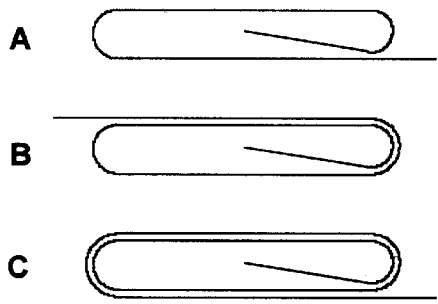
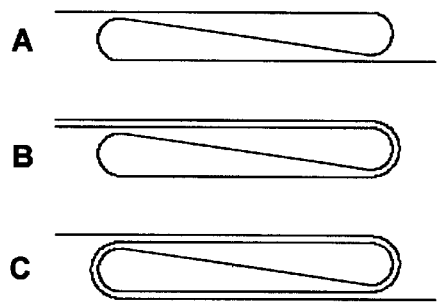
FIG. 7
FIG. 8

COMPACT MICROCHANNEL SYSTEM

The United States Government has rights in this invention pursuant to Contract No. DE-AC04-94AL85000 between the United States Department of Energy and the Sandia Corporation for the operation of the Sandia National Laboratories.

BACKGROUND OF INVENTION

Microchannel devices are finding increased use in the separation, identification and synthesis of a wide range of chemical and biological species. Employing transverse channel dimensions in the range from a few microns to about one millimeter, such systems may permit the miniaturization and large-scale integration of many chemical processes in a manner analogous to that already achieved in microelectronics. Applications for microchannel devices now under development include such diverse processes as DNA sequencing, immunochromatography, the identification of explosives, identification of chemical and biological warfare agents, and the synthesis of chemicals and drugs.

In addition to the potential for large-scale integration, the small physical scales of microchannel devices offer a few inherent advantages over their traditional macro-scale counterparts. Traditional chromatographic separations are usually performed in packed columns. The role of the packing is to provide a stationary phase having a large specific surface area for the adsorption of chemical species. Since various chemical species have different absorption probabilities and residence times on the stationary phase, they move with different speeds through the column and thus exhibit a range of arrival times at the column exit. Although larger surface areas provide better separation between arrival times, the use of packing materials causes nonuniformity of the fluid motion. This results in hydrodynamic dispersion of the solute bands or peaks used to distinguish the species. The benefit of the packing material is thus partially offset by the detriment of increased dispersion. This compromise can be avoided at the smaller scale of microchannel devices. Since the specific surface area of a tube or channel is inversely proportional to its minimum transverse dimension, microchannel columns may provide the required surface area without any need for a packing.

One promising method of microchannel separation is electrochromatography in which electric fields are used to drive electroosmotic fluid motion. Such fluid motion results from the applied electric field acting on charges in the electric Debye layer adjacent to the tube or channel walls, inducing a shear stress very near the boundary of the interior fluid. Electroosmotic flows offer two important benefits over pressure-driven flows for the small physical dimensions characteristic of microchannel devices. First, fluid speeds in electroosmotic flows are independent of the transverse tube or channel dimension over a wide range of conditions, making this technique extensible to extremely small physical scales. In contrast, pressure-driven flows require a pressure gradient that increases inversely with the square of the minimum transverse dimension to maintain a given fluid speed.

Another promising approach to micro-scale chemical analysis is electrophoretic separation. Here the carrier fluid may be either moving or nearly stationary, and an applied electric field is used to drive ionic species through a gel or liquid. Separation occurs because the ion speeds depend on the unique charge and mobility of each species. Provided that the applied field is uniform across the tube or channel cross-section, all ions of the same charge and mobility move at the same speed and so progress along the column without any induced dispersion. Such motion is analogous to the flat velocity profile of an electroosmotic flow, and the various species thus again exhibit unique arrival times at the column exit. Like electrochromatographic processes, electrophoretic separations may be severely degraded by diffusion or dispersion. In the latter case, however, dispersion may arise not only from nonuniformity of the carrier fluid speed but may also arise directly from nonuniformity of the electric field across the column cross-section.

Although species motion in both electrophoretic and electroosmotic transport may be relatively free of both diffusive and dispersive spreading in straight tubes or channels having parallel walls, any local variation in the fluid speed or local field strength introduces dramatic skewing of an otherwise flat interface or species band. Such skewing is known to occur within a separation structure wherein the fluid channel includes bends, or "turns," typically used to extend the length of the channel within a fixed area. Skewing is induced along the radius of the turn because the fluid moving along the outer radius of a turn must travel further than that moving along the inner radius. This difference in path length is compounded by the electric field gradient which is greater along the shorter inner radius, resulting in a greater fluid speed along the shorter path. Thus, an initially flat interface will be severely skewed in passing through a turn. Moreover, because transverse diffusion quickly redistributes solute concentrations across the channel, such skewing is irreversible, and the net effect of transport through any turn or other junction is a large and permanent broadening of any solute peak or interface. As a result, separations are presently performed in straight channels that are limited in length by the maximum substrate dimension. This restriction limits the separation between peaks traveling at different speeds and, so, limits the resolution of separation devices.

Turns are a well-known source of dispersive band spreading in microchannel systems employing electrokinetic species transport. This spreading impairs performance in separation processes, as well as in routine sample transport where the integrity of a band or interface is desired. As a result, turns are often avoided in microchannel system design, especially in the layout of separation columns.

Several previous studies have examined the character and extent of band spreading in turns. Kasicka, et al. (Electrophoresis, v16, 1995, pp. 2034–2038) analyzed the effects of capillary coiling on capillary zone electrophoresis. This study focused on cases in which transverse diffusion is negligible, and the authors obtained closed-form expressions describing the increased variance of the species distribution induced by a turn. Culbertson, et al. (Anal. Chem., v70, 1998, pp. 3781-3789) investigated several sources of dispersion in microchannel devices. As part of this study, they collected a large set of data on the increased variance of a species band downstream of a turn. They also developed a physically-motivated expression describing the increased variance, taking into account both diffusive and convective species transport. More recently, Griffiths and Nilson (Anal. Chem., v72, 2000, pp. 35473–5482) derived a closed-form expression for the increased band variance induced by a turn. This expression was obtained from solutions to the transport equations in the limits of low and high Peclet numbers, again taking into account both diffusion and convection as appropriate.

A few previous studies also have dealt specifically with remedies to turn-induced spreading. Paegel, et al.( Anal. Chem., v72, 2000, pp. 3030–3037) proposed narrowing the channel width upstream of a turn followed by widening the channel once the turn is completed. This approach takes advantage of the fact that the dispersive portion of the increased band variance due to a turn is proportional to at least the square of the channel width. Reducing the channel width throughout the span of the turn thus reduces band spreading. By properly sizing the length and extent of the tapered sections before and after the turn, the authors demonstrated separation efficiencies in folded columns approaching those of a straight separation column of equal length. In contrast, Griffiths and Nilson (Anal. Chem., v73, 2001, pp. 272–278) developed low-dispersion turns based on geometries that counter-rotate the band before and after the turn. These low-dispersion geometries, discerned by means of computer optimization, yield an increased band variance two to three orders of magnitude below that of an equivalent conventional turn, while requiring only moderate constriction of the channel width.

Although special turn geometries offer very significant improvement over conventional turns of similar radius, such enhanced performance is not always required. Large-radius turns of fixed channel width may yield satisfactory performance, so long as the Peclet number is sufficiently small. Recognizing this fact, Culbertson, et al. (Anal. Chem., v72, 2000, pp. 5814–5819) devised a spiral separation column having a large turn radius. This spiral geometry provides a means to construct a very long column within a relatively small chip area, despite the large turn radius. These authors, therefore, successfully demonstrated separation efficiencies that were degraded only slightly by the spiral geometry for a channel width of 40 μm, a minimum turn radius of about 16 mm and Peclet numbers up to about 400.

SUMMARY OF INVENTION

We have examined the spreading of a species band traversing a two-dimensional microchannel turn and an adjoining straight channel segment. The width of the turn and straight segment are assumed to be uniform. Closed-form solutions are obtained describing the minimum turn radius such that dispersive band spreading in the turn is negligible compared to the overall spreading due to diffusion in the turn and straight segment. This minimum radius depends in general on the channel width, included turn angle, the Peclet number and the length of the straight channel segment.

We find that a straight channel segment adjoining a turn significantly reduces the minimum turn radius, provided that the segment length is sufficient: some reduction in the minimum radius can be obtained even when the straight segment length is smaller than the turn radius. Folded separation columns containing straight channel segments may thus employ turns having radii smaller than the minimum radius for a spiral geometry, without degrading the resolution of separation processes.

Based on these results, we have devised new geometries for the compact layout of separation columns. These rely on the benefit of using straight channel segments in conjunction with turns in order to reduce the turn radius. The first geometry is a pleated column, similar to a conventional folded column, in which opposing turns are overlapped to reduce the occupied chip area by about a factor of two below that required for the conventional folded geometry. The second and third are coiled and double-coiled geometries in which the turns are nested. The coiled column has one end that terminates within the coil, while both ends of the double-coiled column terminate outside. Using the double-coiled geometry, a separation column having a 40 μm width and 210 mm length can be placed in a region just 13 by 42 mm. The total length can be extended by about 100 mm for each 2 mm increase is the width and height of this region. The performance of this column is comparable to that of a straight column of equal length for Peclet numbers up to 400.

BRIEF DESCRIPTION OF FIGURES

FIG. 5. Scaled minimum turn radius as a function of the scaled straight segment length. Increasing the straight segment length always reduces the minimum turn radius. Horizontal line at $r^*/P_e=\sqrt{1/3}$ is the approximation of Eq. (9) for $L^* \to 0$.

FIGS. 6A and 6B. Conventional folded column (6A) and pleated column (6B). Pleated column permits roughly a 50% reduction in the area occupied. The pleated pattern may be repeated indefinitely to obtain columns of any length desired.

FIG. 7A, 7B, 7C, and 7D. Sample coiled columns. Straight channel segments enable the use of relatively small turn radii, while the nested geometry provides good utilization of chip area. Extending the length of the coiled column does not significantly increase area occupied.

FIG. 8A, 8B, 8C, and 8D. Double-coiled columns. A sample entering either end progresses toward the coil interior, then away from the interior along interleaved sets of straight column segments and nested turns. Both column ends terminate outside the coil.

DETAILED DESCRIPTION OF THE INVENTION

General

Figure 1:
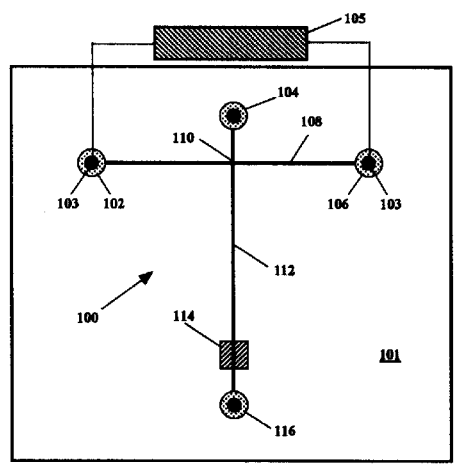
FIG. 1. Shows a schematic of a simple prior art separation system employing a straight separation channel.

The present invention is directed to the compact and efficient layout of columns for microchannel devices used in synthesis and analysis of chemical and biological species. These microchannel devices can be employed for both electrochromatographic and electrophoretic separations, as well as pressure-driven chromatographic separation. The devices are further applicable to microfluidic systems employing either electroosmotic or pressure-driven flows for sample transport, reaction, or synthesis. The present invention is applicable to all channel depths and to a range of channel cross sections including, for example, rectangular, trapezoidal and triangular. The present invention also does not require variable channel depth either along or across the channel.

Microchannel devices typically include multiple transport channels interconnected with one another and with one or more fluid reservoirs. The reservoirs serve both as a means for introducing chemical samples into the system and as a convenient location for electrodes connected to an electric controller. This controller is used to apply electrical potentials that induce electroosmotic or electrophoretic transport along the channels. Since the transport speed of differing species depends on their adsorption characteristics and relative ratios of ion charge to mobility, microchannel devices are commonly used to perform chemical or biological separation processes. The arrival of separated species peaks or bands is monitored at channel outlets, usually by optical detectors. The timing and intensity of the detector response is then used to infer the composition of the sample under analysis.

Microchannels generally have at least one internal transverse dimension that is less than 1 mm, typically ranging from about 0.1 $\mu$m to 500 $\mu$m. Axial dimensions of these microchannels may reach to 10 cm or more. A network of channels and reservoirs is fabricated on a planar substrate by etching, injection molding, embossing or stamping. Lithographic and chemical etching processes developed by the microelectronics industry are now used routinely to fabricate microchannel networks in silicon, polysilicon, glass, and quartz substrates wherein the substrates have lateral dimensions ranging up to tens of centimeters. Similar etching processes are also used to fabricate microchannel devices in any of a number of polymeric substrates such as polymethylmethacrylate (PMMA), polycarbonate, acetal resin homopolymer (Delrin™), polytetrafluoroethylene (Teflon™), polyvinylchloride (PVC), polysulfone, and polydimethylsiloxane (PDMS). However, mass production of microchannel devices is more efficiently performed by stamping, embossing or injection molding of polymeric materials using tools or molds that have been produced by lithography and etching or by electroforming as in the LIGA process. After fabrication of a microchannel network on a planar substrate it is mated with one or more planar sheets that seal channel tops and/or bottoms while providing access holes for fluid injection and extraction ports as well as electrical connections.

FIG. 1 schematically illustrates a representative chemical analysis system, 100, fabricated on a planar substrate, 101. The fluid reservoirs 102, 104, 106, and 116 have access ports (not shown) that permit injection or extraction of fluid through the top or bottom faces of substrate 101. Similar ports are also used to insert electrodes 103 and tubes (not shown) used to control electric potentials or hydrostatic pressures within the reservoirs. In the system of FIG. 1, a fluid sample is initially injected into reservoir 102 and then transported through channel 108 by raising the electric potential (or pressure) of reservoir 102 above that in reservoir 106 by adjusting power or hydrostatic supply 105. After completing this step, the separation channel, 112, contains a small volume of the sample within the junction, 110. The small sample is then moved forward along the separation channel, 112, by raising the electric potential (or pressure) in reservoir 104 above that in 116. Because of differences in surface adsorption, ion charge, and ion mobility, different species within the sample move along the separation channel at different speeds. As a result, the sample separates into a series of bands that are detected as they pass through a detection device, 114, located toward the end of the channel. The contents of the sample are inferred from the observed arrival times of the separated bands.

Chemical or biological samples are transported through microfluidic devices by electroosmosis, electrophoresis, or by pressure driven flow. In electroosmosis, bulk flow is induced by applying an electric field to a fluid containing a net mobile charge within the Debye layers adjacent to channel surfaces. In electrophoresis, by contrast, there is no bulk motion of the fluid or gel contained within the separation channels. Instead, the applied electric field causes migration of ionic species through a substantially stationary fluid or gel, at speeds that depend on the ion charges and mobilities of the species. Both of these processes may occur simultaneously when an electric field is applied to a fluid, though one is usually dominant. In pressure driven flow, bulk motion is induced by applying a pressure difference between channel ends. The present invention is applicable to all electroosmotic and electrophoretic devices and to pressure driven devices having channel depths small compared to their widths.

To obtain the desired species separation, the separation channel 112 may be filled with a separation matrix such as gel or a porous or granular material. Gels are often employed as the stationary phase in electrophoretic separations. Porous and granular materials are often used in chromatographic separations to increase the surface area and provide a specialized adsorption surface known to selectively retard particular species. Alternatively, the separation matrix used to increase surface area may be a small-scale pattern or array of obstacles fabricated within the channel. The selectivity of these fabricated surfaces may also be altered by coating or chemical processing. The present invention is likewise applicable to channels filled with a separation matrix for both electrokinetic and pressure-driven species motion.

Figure 2:
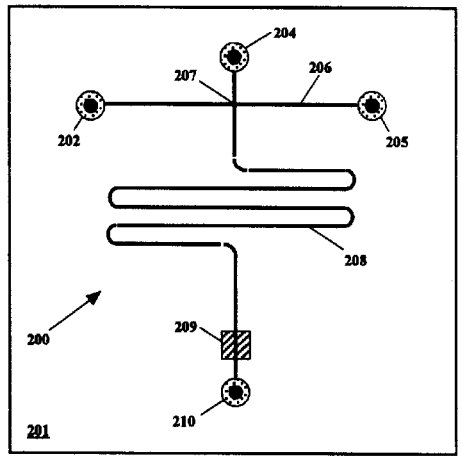
FIG. 2. Shows a schematic of a prior art separation system employing a folded, serpentine separation channel employing multiple turns.

FIG. 2 illustrates a slightly more complex chemical analysis system, 200, as is described in U.S. Pat. No. 6,186,660. The system includes a folded or serpentine separation channel, 208, fabricated on a planar substrate, 201. In analogy to the discussion of FIG. 1, the sample is introduced into reservoir 202, and transported through channel 206 toward reservoir 205. Then, to move the sample through the system, an electric potential or hydrostatic pressure in reservoir 204 is raised above that in reservoir 210. As a result, the volume of sample residing in junction, 207, is transported through the folded separation channel, 208, toward the detector, 209.

The serpentine separation channel, 208, is folded back upon itself to permit fabrication of a long channel on a small substrate, or within small areas of a larger substrate. Long separation channels are beneficial in producing wider spacing between species bands moving at differing speeds along the channel. However, any dispersion or spreading of species bands reduces the ability to distinguish closely spaced peaks.

In addition to the separation devices shown in FIGS. 1 and 2, microfluidic devices can also be used to perform a broad range of chemical reaction, mixing, and synthesis processes currently performed at larger scales. Such devices may involve long channels used, for example, in reactions between several species. As in separations, many of the chemical processes performed by these devices may be degraded by dispersion of compositional interfaces. Thus, the broader utility of the present invention is to provide the compact and efficient layout of long folded channels that do not degrade system performance for a broad range of microchannel devices.

Mathematical Model

Figure 3:
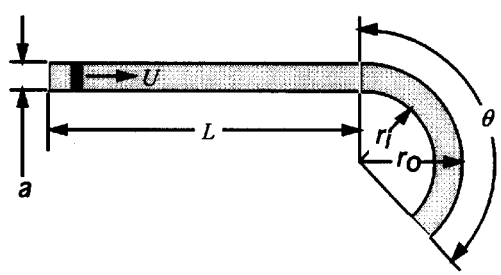
FIG. 3. Schematic of a turn and straight channel segment. The turn radius and channel width are assumed to be constant. A sample band travels along the straight channel segment at a fixed speed U FIG. 4. Minimum normalized turn radius for negligible turn-induced band spreading. For a given turn angle, the minimum radius depends on both the Peclet number, $P_e$, and length of the straight channel segment adjoining the turn, $L^*=L/a$.

Consider the structure illustrated in FIG. 3 comprising a straight channel segment of length, L, connected to a curved segment, known as a "turn," of arbitrary included angle, $\theta$.

The geometry of FIG. 3 represents a single turn and an associated straight segment from a folded column. The channel width, a, is assumed to be uniform through the turn and through the straight segment, and the mean radius of the turn, $\bar{r}$, is also assumed to be constant.

In a previous study, (Anal. Chem., v72, 2000, pp. 35473–5482), we derived a closed-form expression describing the increased variance of a sample band as it spreads in traversing a turn. The governing transport equations were solved analytically to obtain the increased variance of a species band or compositional interface in the limits of low and high Peclet numbers. These two results were then combined to yield a single expression applicable to all Peclet numbers. The result obtained is $$\left(\frac{\sigma}{a}\right)^2 = \frac{\theta^2 P_e}{15r^* + eP_e} + \frac{2r^*\theta}{P_e} \qquad (1)$$

where $\sigma^2$ is the total increased variance of the band resulting from transport through a turn, a is the channel width, $\theta$ is the included turn angle, and $r^* = \bar{r}/a = (r_i + r_o)/2a$ is the normalized mean turn radius.

The Peclet number appearing in Eq. (1) is a dimensionless parameter given by $P_e = Ua/D$ where U is the uniform mean fluid or species speed well ahead of the turn, and D is the species diffusivity. This parameter indicates the relative magnitudes of convective and diffusive transport rates. Diffusive transport is relatively unimportant when the Peclet number is large, but is dominant when Peclet numbers are small. Peclet numbers for liquid-based microchannel systems involving small species molecules typically range from order ten to several hundred. Those for gel-based systems, or systems involving very large molecules, typically range from a few hundred to several thousand. The Peclet number is also related to the theoretical plate height of a separation column. The value is given by $P_e 2a/h$, where h is the minimum possible plate height based on diffusive spreading alone.

Note that Eq. (1) describes the total turn-induced variance and that this total results from two contributions. The first contribution, given by the first term on the right, is that due to nonuniform species speeds associated with the curved turn geometry. The second contribution, given by the second term on the right, is the increased variance due to streamwise diffusion during the period that the band resides in the turn. This contribution is proportional to the arc length of the turn and is the same as that due to diffusive spreading in a straight channel segment of equal length.

The governing equations leading to Eq. (1) were developed in the context of neutral species transport in electroosmotic flow. However, these governing equations also describe the transport of a single charged species in electrophoretic motion in a stationary phase. That is, in both cases the species flux varies linearly with both the concentration gradient and the electric field. For electroosmotic flow, the local species flux is $J = -D\nabla c - (\epsilon\zeta\nabla\phi/\mu)$ and, the electrophoretic flux is $J = -D\nabla c + vzF\nabla\phi$.

As such, solutions to the problem of electroosmotic flow also apply to that of electrophoresis, provided that both problems are properly normalized. Further, similar equations also govern species transport in some pressure-driven flows. In both porous materials and open channels having a very small aspect ratio, the local velocity of an incompressible fluid is proportional to the pressure gradient at low Reynolds numbers, and the pressure field is governed by the Laplace equation. The discussions that follow thus also apply to pressure-driven flows in these special cases.

A simple physical basis for determining the effect of a turn on overall performance is to compare the dispersive portion of turn-induced spreading with that spreading due to diffusion alone. The diffusive spreading depends only on the species diffusivity and residence time and thus is the same regardless of whether a channel is straight or curved. Further, this diffusive spreading provides an absolute minimum bound on the extent of band spreading for a given length of travel. This comparison thus provides a rigorous basis for evaluating the detrimental influence of the turn. If the dispersive spreading is much smaller than the overall spreading due to diffusion, then the curved geometry of the turn will have little effect on the final state of the band.

In the present study, we consider the diffusion occurring in both the turn and in a straight channel segment adjacent to this turn. The induced variance for diffusion in the straight segment is $\sigma^2 = 2Dt$, where $t = L/U$ and L is the length of the original channel straight segment. Rearranging slightly, this may be written in the form $$\left(\frac{\sigma}{a}\right)^2_{diff} = \frac{2L}{P_e a} = \frac{2L^*}{P_e} \qquad (2)$$

where the dimensionless length $L^*$ is simply the length of the straight segment normalized by the channel width.

The increased variance due to diffusion in the turn is given by the second term on the right of Eq. (1), so the total increased variance due to diffusion in both the turn and straight segment may be written as:

$$\left(\frac{\sigma}{a}\right)^2_{diff} = \frac{2L^*}{P_e} + \frac{2r^*\theta}{P_e} = \frac{2}{P_e}(L^* + r^*\theta) \qquad (3)$$

This requires that the channel width is uniform, so that the mean species speed U and the Peclet number are the same in the turn and straight channel segment. Note that the total increased variance due to diffusion is proportional to the total length of travel through the turn and straight segment combined since $r^*\theta$ is the normalized mean arc length of the turn.

The increased variance due to dispersion in the turn is given by the first term on the right of Eq. (1). That is, $$\left(\frac{\sigma}{a}\right)^2_{diff} = \frac{\theta^2 P_e}{15r^* + 3P_e} \qquad (4)$$

Again, the Peclet number here is the same as appears in Eq. (3) if the channel width is constant. Now, the condition for negligible turn-induced spreading may be written as $$\left(\frac{\sigma}{a}\right)^2_{disp} \ll \left(\frac{\sigma}{a}\right)^2_{diff} \qquad (5)$$

From a practical perspective, this inequality is satisfied when the turn-induced spreading is at least an order of magnitude smaller than that due to diffusion alone. Taking this as the criterion for acceptable turn performance, the inequality above can be rewritten as $$\frac{\theta^2 P_e}{15r^* + 3P_e} \leq \frac{1}{10}\left[\frac{2}{P_e}(L^* + r^*\theta)\right] \qquad (6)$$

From the form of this expression, we see that the roots of the equality satisfy the inequality when these roots are viewed as the minimum turn radius, minimum straight segment length or maximum Peclet number. Equation (6) possesses only one positive root for the normalized turn radius given by:

$$r^* \geq \frac{P_e + 5L^*}{10\theta}\left[\sqrt{1 + \frac{20P_e(5\theta^2 P_e - 3L^*)}{3(P_e + 5L^*)^2}} - 1\right] \quad (7)$$

The equality in this expression thus describes the minimum turn radius that will yield negligible turn-induced dispersion, as defined by Eq. (6) above. Any larger radius will give a turn-induced increased band variance that is more than an order of magnitude smaller than the increased variance due to diffusion in the turn and straight segment combined.

Note that the dimensional form of Eq. (7), yielding $\bar{r}$ rather than $r^*$, can be obtained simply by replacing $L^*$ with $L$ and replacing the Peclet number, $P_e$, with the product $aP_e$. In addition, the Peclet number in either the dimensionless or dimensional form of Eq. (7) may be replaced by the term $2a/h$, where $h$ is the minimum possible plate height of a column.

Finally, note that $L^*$ physically represents the overall straight segment length associated with a single turn. It does not matter whether this segment is upstream or downstream of the turn. Similarly, it is unimportant whether this is a single segment, as shown in FIG. 3, or two segments of the same total length. Segments upstream and downstream of a turn can be added to yield the overall $L^*$ associated with the turn.

Values of the minimum turn radius calculated using Eq. (7) are plotted in FIG. 4 as a function of the Peclet number for $\theta=\pi$ and several values of $L^*$. Features of this plot are described in the context of the following discussions.

The case of no adjoining straight channel segment is of special interest because this provides a simple upper bound on the minimum turn radius. The addition of a straight channel segment always yields a minimum radius that is below this bound. In this limit, the minimum turn radius given by Eq. (7) reduces to $$r^* \geq \frac{\sqrt{9 + 300\theta^2}}{30\theta}P_e \text{ for } L^* \to 0 \quad (8)$$

Figure 4:
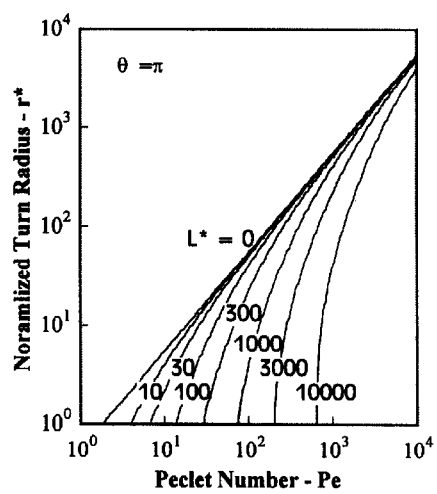

This result appears in FIG. 4 as the straight line denoted $L^*=0$. Eq. (8) can also be approximated by:

$$r^* \geq \frac{P_e}{\sqrt{3}} \approx 0.58P_e \text{ for } L^* \to 0 \quad (9)$$

for included turn angles $\theta \geq \pi/2$. This approximation is conservative for all included turn angles of practical importance. It over-estimates the minimum radius by about 12% for $\theta=\pi/2$ and by less than 6% for $\theta \geq \pi$. In this limit of no adjoining straight length segment, the minimum normalized turn radius is thus strictly proportional to the Peclet number and nearly independent of the included angle of the turn for most turns of practical interest.

In the opposite extreme of very large $L^*$, the minimum radius given by Eq. (7) yields negative values for sufficiently small Peclet numbers. This result is simply a mathematical artifact and indicates only that turn-induced dispersion can exceed the high Peclet number limit of $\theta 2/3$ without violating Eq. (7). In practice, however, the normalized turn radius must be at least one-half since the mean radius must by necessity remain at one-half the channel width when the inner radius vanishes. This limitation thus provides the minimum length of the straight channel segment for which all turns satisfy Eq. (7). For lengths above this minimum, the turn will not significantly contribute to overall band spreading regardless of the turn radius. The condition for this may be expressed as:

$$r^* = \frac{1}{2} \text{ for } L^* \geq \frac{5(4P_e - 3)\theta^2 - 6\theta P_e}{5(2P_e + 5\theta)} \quad (10)$$

For $\theta \geq \pi/4$ and Peclet numbers $P_e \geq 25\theta$, is expression is well approximated by:

$$r^* = \frac{1}{2} \text{ for } L^* \geq \frac{5\theta^2 P_e}{3} \quad (11)$$

The condition in Eq. (11) gives $L^* \geq 16.4P_e$ for $\theta=\pi$ or, equivalently, $P_e \leq 0.061L^*$. These values of the Peclet number correspond roughly to the intercepts of each of the plurality of curves shown in FIG. 4 with the horizontal axis of the figure.

Between the extremes of small and large straight segment lengths, the general behavior of Eq. (7) can be discerned by reconsidering the form of this expression. We find upon inspection that this result can also be written in terms of a scaled minimum turn radius, $r^*/P_e$, that is a function only of the included turn angle and a scaled straight segment length, $L^*/P_e$. The independent influences of $L^*$ and $P_e$ are thus eliminated, and the result is simply:

$$\frac{r^*}{P_e} \geq \frac{1 + 5L^{}}{10\theta}\left[\sqrt{1 + \frac{20(5\theta^2 - 3L^{})}{3(1 + 5L^{**})^2}} - 1\right]^2 \quad (12)$$

where $L^{**}=L^*/P_e=Lh/2/a^2$.

Values of the scaled minimum turn radius computed using Eq. (12) are shown in FIG. 5 for included angles $\theta=\pi/4, \pi/2$ and $\pi$. Consistent with Eq. (8), we see that the scaled minimum turn radius depends only on the included turn angle when the scaled straight segment length is small. This is indicated by the horizontal asymptotes on the left of the figure; the value of each asymptote is simply the minimum radius given by Eq. (8) divided by the Peclet number. The additional horizontal curve labeled $r^*P_e=\sqrt{1/3}$ represents the approximation specified in Eq.(9).

We also see that the minimum radius is reduced from these asymptotes only when the scaled straight segment length is sufficiently large. Expanding Eq. (12) for small $L^{**}$, we find that the minimum scaled segment length needed to obtain a 5% reduction in the turn radius is:

$$\frac{L^*}{P_e} \geq \frac{\theta^2\sqrt{9 + 300\theta^2}}{\left[3 + \sqrt{9 + 300\theta^2}\right]^2} \approx \frac{\theta}{10\sqrt{3}} \approx \frac{r^*\theta}{10P_e} \quad (13)$$

Values of this minimum length and the corresponding minimum turn radius are indicated in FIG. 5 by the three small dots. The first approximation on the right of Eq. (13) is based on the assumption that $\theta^2 >> 3/100$. Values of the minimum length computed using this approximation are shown in FIG. 5 by the short vertical lines crossing the solid curves; these values are correct to within 20% for $\theta \geq \pi/2$. The second approximation on the right of Eq. (13) is obtained by the substitution $\sqrt{9 + 300\theta^2} \approx 30r^*/(P_e+3)$ based on Eq.(8). This approximation, shown in FIG. 5 by the three dashed curves, is correct to within 13% for $\theta \geq \pi/4$. We thus conclude that a straight channel segment may be beneficial in reducing the minimum radius when the length of the segment exceeds about one-fourth of the minimum turn radius. This conclusion is applicable to all included turn angles of practical importance and is independent of the Peclet number.

The minimum turn radius falls rapidly for straight segment lengths greater than that given by Eq. (13). For a length ten times larger than this minimum value, the minimum radius is reduced by a factor of about 1.6 below the asymptotic value for $L^* \to 0$. At twenty times the minimum length, the minimum radius is reduced by about a factor of 3. For still greater lengths, the scaled minimum radius falls to zero as the scaled straight segment length approaches $L^*/P_e \to 5\theta^2/3$. This occurs when the length is a factor of $50\theta/\sqrt{3}$ above the minimum given by Eq. (13).

Some care must be exercised in applying these results when a channel contains multiple turns. The high Peclet number portion of Eq. (1) is not dispersive in the classical sense and produces a downstream distribution of the species concentration that varies both along and across the channel. The consequence of this is that the turn-induced increased variance may not be additive for multiple turns.

This apparent discrepancy results from an implicit assumption in deriving Eq. (1) that the profile of the species distribution approaching the turn is uniform across the channel. This assumption may be violated when two turns are closely coupled. In this case, the species distribution of the profile entering the second turn in the pair is highly nonuniform across the channel if the Peclet number is large. As a result, the increased variance due to a 360° turn is twice that of two 180° turns when the Peclet number is large and both 180° turns rotate sample motion in the same direction. Similarly, the total increased variance due two coupled 180° turns may be less than that of a single 360° turn if the two turns rotate in opposing directions.

The increased variance due to multiple turns is simply additive for diffusive spreading and turn-induced spreading at low Peclet numbers. This is because the species distribution just downstream of a turn is uniform across the channel in both of these cases, so the band is also uniform across the channel as it enters the next turn.

The increased variance due to multiple turns is also additive at high Peclet numbers if two or more turns are linked by a straight channel segment of sufficient length. In this case, transverse diffusion during sample motion along the straight segment redistributes species concentrations such that the species distribution is once again uniform across the channel as the band enters the second turn. The condition for uniform redistribution is roughly given by $Dt \geq a^2$ where $t=L/U$. Rewriting this expression in normalized form yields $$L^* \geq P_e \qquad (14)$$

Note that Eq. (14) is slightly more restrictive than Eq. (13) for $\theta=\pi$ and that both of these should be satisfied. In practice, however, Eq. (13) specifies only the smallest straight segment length providing any significant reduction in the minimum turn radius. Large reductions in the minimum radius require significantly larger lengths, so Eq. (14) will likely be satisfied for most geometries of practical importance.

We now examine several sample problems to illustrate the use of these results. First, consider the problem of a spiral column as presented by Culbertson et al. (Anal. Chem., v72, 2000, pp. 5814–5819). Their column consisted of two full turns having a minimum radius of 16 mm. The channel width was $a=40$ μm, and the total column length was 220 mm. At an applied electric field of $E=120$ kV/m, they reported a plate height of about $h=0.2$ μm. This corresponds to a Peclet number of $P_e=2a/400$. This is the largest Peclet number for the conditions reported in their study and so represents the most stringent condition for determining the minimum spiral radius.

For spirals spanning at least one full turn, the minimum radius is well approximated by Eq. (9) describing the case of no adjoining straight channel segment. The minimum normalized radius is thus proportional to the Peclet number and independent of the total number of turns. The dimensional turn radius is therefore proportional to the product of the mean species speed and square of the channel width and inversely proportional to the diffusivity.

Eq. (9) yields $r^*=\bar{r}/a=230$ for a Peclet number of $P_e=400$, or $\bar{r}=9.2$ mm for a channel width of $a=40$ μm. This computed minimum radius thus agrees fairly well with the minimum radius of $\bar{r}=16$ mm used in the Culbertson study. They indicate that the turn-induced spreading contributes at most about 5% to the overall variance of their measured species distribution, so their larger radius is consistent with the less stringent requirement of 10% used here in developing Eq. (7) and (9). Equivalently, we would conclude that their apparatus should also perform well up to a Peclet number of about 800.

Next, we consider the problem of folding an electrophoretic separation column using multiple turns with adjoining straight segments. The channel width and straight segment length are $a=40$ μm and $L=30$ mm. These yield $L^*=L/a=750$. Now, the Peclet number for a purely electrophoretic processes is $P_e=Ua/D=avzFE/D \approx azFE/RT$, where $RT/F \approx 25$ mV. Given a charge number of $z=2$ and an applied field of 120 kV/m, the Peclet number is $P_e \approx 400$. This folded-column problem is thus the same as the spiral problem previously addressed, except that adjoining straight segments are now also considered in the analysis.

Given these conditions, Eq. (7) yields $r^*=122$ mm for an included angle of $\theta=\pi$. This is equivalent to $\bar{r}=4.9$ mm for $a=40$ μm. Note that this value is about half the minimum radius previously obtained for a spiral. Moreover, increasing the straight segment length from 30 to 60 mm reduces the minimum radius to just to $\bar{r}=2.9$ mm. The benefit of using straight channel segments in conjunction with turns is thus, readily apparent.

For a straight segment length of $L=30$ mm and a minimum turn radius of to $\bar{r}=4.9$ mm, a separation column having a total length of 120 mm can be folded onto a region just 40 mm by 20 mm. Expanding this region to 40 mm by 40 mm permits a total column length of 210 mm. This length and area are comparable to those of the spiral problem previously examined.

These sample problems have addressed only electrophoretic transport. The solutions do, however, also describe the transport in electroosmotic flows. The only difference between these two cases is that the Peclet number for electroosmotic flows must be calculated using the channel width, a known fluid speed and a measured or estimated diffusivity. For example, a fluid speed of $U=5$ mm/s, a channel width of $a=40$ μm and a molecular diffusivity of $D=5\times10^{-10}$ m$^2$/s also yields $P_e=Ua/D=400$ as in the sample calculations above. The minimum turn radii for this problem are therefore the same as those given above.

Preferred Embodiment—Pleated and Coiled Columns

Both spiral and conventional folded columns offer advantages and drawbacks from a practical perspective. While spiral columns retain useful chip area in their interior, the minimum spiral radius may still be quite large for a high-performance column operating at high Peclet numbers. Such columns do not take advantage of the benefit of adjoining straight channel segments in reducing the minimum turn radius. Folded columns, on the other hand, can be constructed using relatively smaller turn radii when the straight channel segments are sufficiently long. Even so, conventional folded columns consisting of parallel straight segments joined by multiple turns make very poor use of available chip area. As shown in FIG. 6A, the spacing between the straight segments is twice the turn radius, and this may still be significant at high Peclet numbers. As a practical result, it is generally difficult to fold high-performance columns more than a few times using this conventional approach.

One preferred alternative embodiment to spiral or conventional folded columns is the pleated column shown in FIG. 6B. In a pleated column, the centers of the turns at opposing segment ends are shifted such that the two turns at least partially overlap. Shifting the centers in this way increases the included angle of the turn only slightly, so the turn-induced spreading is not much affected. The benefit of the pleated column is that straight segments are separated, on average, by just over one turn radius. A pleated column thus occupies about half of the area required for a conventional folded column. Equivalently, the overall length of a pleated column may be roughly twice that of a conventional folded column given the same available chip area.

While the area occupied by a pleated column is significantly less than that of an equivalent folded column, the required chip area is still roughly proportional to the product of the total column length and turn radius. This shortcoming is avoided in the coiled column illustrated in FIG. 7. The coiled column consists of several straight channel segments that are joined end-to-end by turns that are nested. These turns are nested in a concentric fashion by increasing the radius of each subsequent (outer) turn. In contrast to pleated and conventional folded columns, these nested turns all rotate sample motion in the same direction.

Figure 7D:
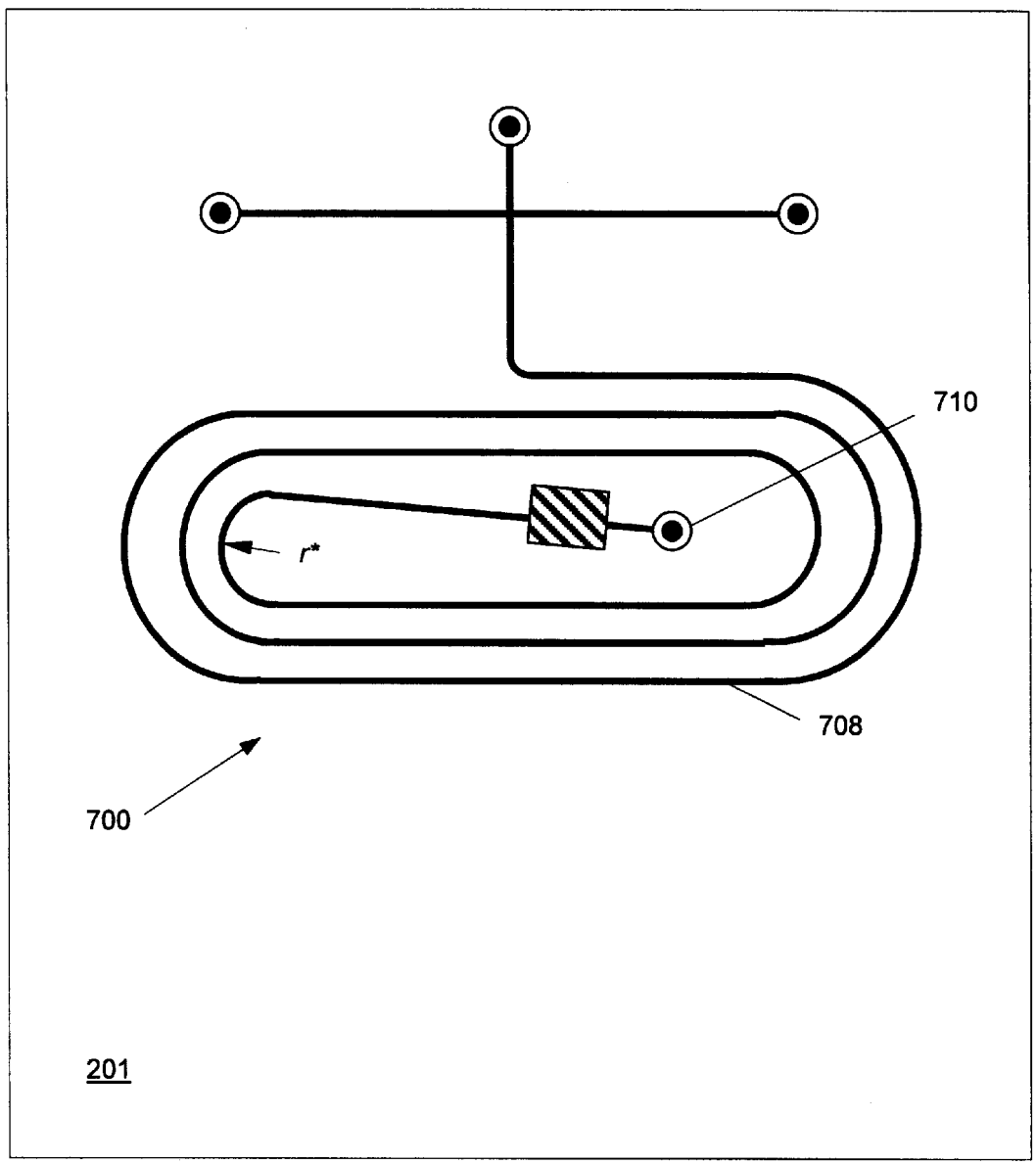

The main advantage of this coiled column is that the required chip area is generally much smaller than that of either a folded or pleated column. As illustrated in FIGS. 7A, 7B and 7C numerous straight segments joined in this manner form a coiled column that occupies only slightly more area than a single fold of the prior art embodiment of FIG. 2. Furthermore, the area occupied by the coiled column grows only in proportion to the product of the straight segment length and the spacing between neighboring segments. As such, a very long column 708 can be placed in a small chip area using this coiled geometry to provide the improved column system 700 illustrates in FIG. 7D. If the minimum turn radius r*, is consistent with Eq. (7), the performance of such a column should be comparable to that of a straight column having an equivalent total length.

One potential limitation of a coiled column, however, is that one end 710 of the column must terminate within the coil. This requires a reservoir, electrode and either an injection junction or detection point be located in this interior region. If the interior is large, as in a spiral, this may not be a problem. Locating reservoirs and other system features inside the spiral is then an effective use of real estate. The coiled column, however, may have turn radii much smaller that those of an equivalent spiral. The interior area of a coiled column is therefore generally smaller, representing less wasted chip area, but this smaller area may also be less useful. One approach to avoiding this potential limitation is the double-coiled column system 800 shown in FIG. 8.

Figure 8D:
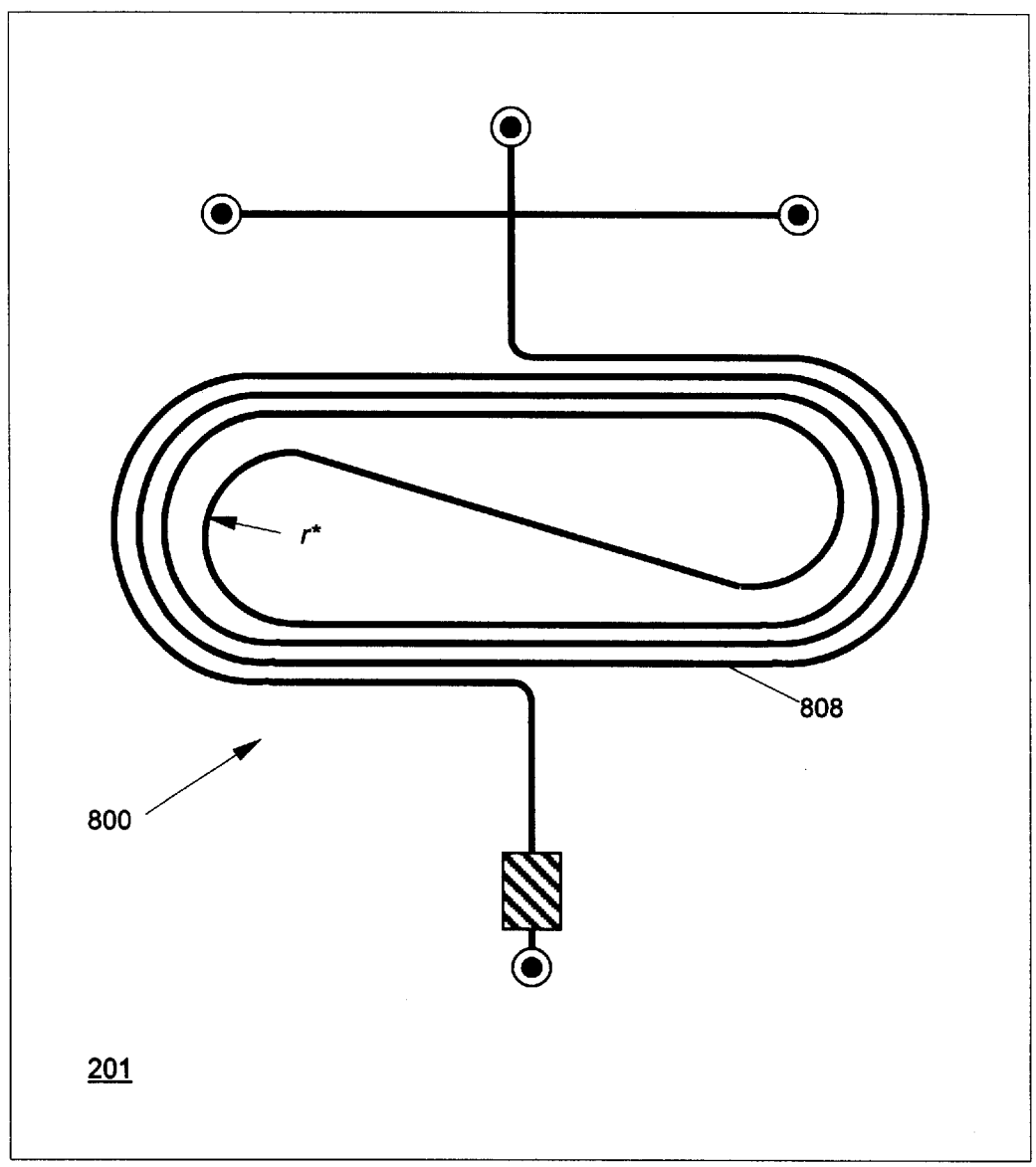

The double-coiled column consists of two coiled segments, each like the coiled columns already discussed. These two coiled segments are interleaved so that the nested turns at the two ends of the coil alternate between the two segments as seen in FIGS. 8A through 8C. The straight channel segments at the top and bottom of each coil similarly alternate between the two. The interior ends of the two coiled segments are joined to form a single continuous column 808 having two ends that terminate outside the coil as can be seen in FIGURE 8D. Again, the turn radius should satisfy Eq. (7), and the straight segment lengths should be at least one-fourth of the radius.

A sample band entering either end of a double-coiled column first progresses toward the interior along one of the coiled segments. At each turn along this first coiled segment, the direction of sample motion is rotated through about 180° and the sign of this rotation is always the same. Once the sample passes through the interior, it progresses toward the exterior along the second coiled segment. Again, each turn along this segment rotates the direction of motion with the same sign, but the sign of this rotation is opposite to that of the first coiled segment.

Both coiled and double-coiled columns offer a significant benefit over both spiral and conventional folded columns. To illustrate this, again consider the problem of a separation column that is 40 $\mu$m wide and operating at a maximum Peclet number of 400. As before, the minimum turn radius given a straight segment length of L=30 mm is $\bar{r}$ 4.9 mm. Allowing 1 mm between each straight segment and nested turn, the coiled column of FIG. 7D provides a total column length of 200 mm in a region of just 13 by 42 mm. The double-coiled column of FIG. 8D provides a total length of 210 mm in a similar region. Overall lengths of both these columns can be increased by about 100 mm for each additional pair of turns and straight segments, while increasing the required region by only 2 mm in each dimension.

The examples shown here for pleated, coiled and double-coiled channels all illustrate convolutions of just one channel. All of these geometries can also be used with multiple parallel channels. The patterns presented here need only be considered as the centerline of a bundle of several parallel channels. These geometries also all show individual turns of constant radius. For coiled and double-coiled columns, in particular, individual turns having a varied radius may also be employed. Similarly, these new geometries based on turns and straight channel segments can be approximated by smoothly-varying ovals or ellipses having roughly the same proportions.

I claim:

1. A fluid separation device comprising:
   a body structure having at least one separation column fabricated therein, said at least one separation column for transporting a fluid therein, and wherein said at least one separation column comprises a fluid channel having first and second ends and an overall length, said fluid channel coiled upon itself in a plurality of connected loop segments to provide a channel coil, each of said loop segments concentrically nested such that none of said loop segments cross wherein each of said plurality of loop segments further comprise straight portions connected end-to-end by curved portions.

2. The device of claim 1, wherein said overall length provides means for causing a fluid sample to separate into a plurality of detectable sample bands as said fluid sample is transported through said fluid channel.

3. The device of claim 2, wherein each straight portion comprises a different length, L, which is shorter than said overall length.

4. The device of claim 2, wherein each of said curved portions comprises a different turn radius, r, said turn radius, r, monotonically increasing in sequence from small to large, wherein said smallest turn radius is at least greater than a minimum turn radius chosen to eliminate a turn induced dispersion in said sample bands.

5. The device of claim 1, wherein said channel coil is coiled in a first direction beginning at an end opposite a first end of a first straight portion such that said first end is disposed within an interior parameter of said channel coil and said second end is disposed external to an outside parameter of said channel coil.

6. The device of claim 1, wherein said channel coil is coiled in a first direction around each end of a first straight portion such that said first and second ends are each both disposed external to an outside parameter of said channel coil.

7. The device of claim 6, wherein said channel coil comprises a double-ended spiral pin-wheel to provide a plurality of nested loops, wherein each of said curved and straight portions comprising each of said nested loops is off-set from each preceding loop by a uniform, incremental distance η, wherein η is greater than of about one channel width.

8. The device of claim 1, wherein said channel coil is first coiled in a first direction and then coiled in a second direction.

9. The device of claim 1, comprising at least a second fluid channel, wherein said second fluid channel intersects said at least first separation column.

10. The device of claim 9, wherein said intersection of said first separation column and said second fluid channel comprises a "T" intersection or a crossing intersection.

11. The device of claim 1, further comprising an electrical control system operably coupled to first and second ends of said first and second fluid channels so as to controllably direct material flow through said first and second fluid channels.

12. The device of claim 1, said first separation column comprising at least one cross-sectional dimension between about 0.1 μm and about 500 μm.

13. The device of claim 1, said first separation column comprising at least one cross-sectional dimension between about 10 μm and about 200 μm.

14. The device of claim 1, said first separation column comprising at least one cross-sectional dimension between about 5 μm and about 20 μm.

15. The device of claim 1, wherein said first separation column comprising a fluid mixing portion, wherein said fluid mixing portion is between about 0.1 mm and 10 mm in length.

16. The device of claim 1, said body structure comprising an aggregation of two or more layers.

17. The device of claim 16, wherein said first separation column is fabricated by producing a groove in a first substrate corresponding to a first of said two or more layers and covering said grove with a second substrate corresponding to a second of said two or more layers.

18. The device of claim 1, wherein said body structure comprises at least one of glass, quartz, silicon, polysilicon, polymethylmethacrylate, polycarbonate, polytetrafluoroethylene, a acetal resin homopolymer, polyvinylchloride, polydimethylsiloxane, and polysulfone.

19. The device of claim 1, comprising one or more fluids in said channel.

20. The device of claim 19, said fluid comprising a Peclet number up to about 800.

21. The device of claim 1, wherein said first channel is one member of an array of interconnected channels disposed on or within said body structure.

* * * * *